US012233253B2

(12) United States Patent
Sullivan

(10) Patent No.: US 12,233,253 B2
(45) Date of Patent: Feb. 25, 2025

(54) WEARABLE CARDIOVERTER DEFIBRILLATOR (WCD) WITH BYSTANDER VOICE INTERACTION

(71) Applicant: WEST AFFUM HOLDINGS DAC, Dublin (IE)

(72) Inventor: Joseph L. Sullivan, Kirkland, WA (US)

(73) Assignee: West Affum Holdings DAC, Dublin (IE)

( * ) Notice: Subject to any disclaimer, the term of this patent is extended or adjusted under 35 U.S.C. 154(b) by 442 days.

(21) Appl. No.: 17/508,637

(22) Filed: Oct. 22, 2021

(65) Prior Publication Data
US 2022/0143388 A1 May 12, 2022

Related U.S. Application Data

(60) Provisional application No. 63/111,957, filed on Nov. 10, 2020.

(51) Int. Cl.
*A61N 1/00* (2006.01)
*A61N 1/04* (2006.01)
*A61N 1/39* (2006.01)

(52) U.S. Cl.
CPC ............ *A61N 1/046* (2013.01); *A61N 1/0484* (2013.01); *A61N 1/3904* (2017.08); *A61N 1/3987* (2013.01)

(58) Field of Classification Search
CPC .............................. A61N 1/046; A61N 1/3904
USPC ............................................................ 607/5
See application file for complete search history.

(56) References Cited

U.S. PATENT DOCUMENTS

| 3,724,455 A | 4/1973 | Unger |
| 4,583,524 A | 4/1986 | Hutchins |
| 4,619,265 A | 10/1986 | Morgan et al. |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |

(Continued)

FOREIGN PATENT DOCUMENTS

| EP | 3380189 B1 | 10/2018 |
| WO | 1998039061 A2 | 9/1998 |
| WO | 2012064604 A1 | 5/2012 |

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

(Continued)

*Primary Examiner* — Nicole F Lavert
(74) *Attorney, Agent, or Firm* — Polsinelli PC

(57) ABSTRACT

In one aspect, an example wearable cardioverter defibrillator (WCD) system implementing the disclosed techniques includes a support structure, the support structure configured to be worn by a subject. The WCD system also includes a consciousness detection module configured to determine whether the subject wearing the support structure is unconscious. The WCD system further includes an interactive bystander module configured to, responsive to a determination that the subject wearing the support structure is unconscious, generate a first voice prompt inquiring as to a presence of a bystander.

18 Claims, 5 Drawing Sheets

(56) References Cited

U.S. PATENT DOCUMENTS

| | | |
|---|---|---|
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny |
| 5,405,362 A | 4/1995 | Kramer et al. |
| 5,474,574 A | 12/1995 | Payne et al. |
| 5,618,208 A | 4/1997 | Crouse et al. |
| 5,662,690 A | 9/1997 | Cole et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder |
| 6,427,083 B1 | 7/2002 | Owen et al. |
| 6,437,083 B1 | 7/2002 | Owen et al. |
| 6,529,875 B1 | 3/2003 | Nakajima |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,548,557 B2 | 10/2013 | Garstka et al. |
| 8,615,295 B2 | 12/2013 | Savage et al. |
| 8,644,925 B2 | 2/2014 | Volpe et al. |
| 8,676,313 B2 | 3/2014 | Volpe et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,089,685 B2 | 7/2015 | Sullivan et al. |
| 9,131,901 B2 | 9/2015 | Volpe et al. |
| 9,132,267 B2 | 9/2015 | Kaib |
| 9,408,548 B2 | 8/2016 | Volpe et al. |
| 9,454,219 B2 | 9/2016 | Volpe et al. |
| 9,592,403 B2 | 3/2017 | Sullivan |
| 9,878,171 B2 | 1/2018 | Kaib |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2006/0173499 A1 | 8/2006 | Hampton et al. |
| 2008/0312709 A1 | 12/2008 | Volpe et al. |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |
| 2014/0046391 A1* | 2/2014 | Cowan ................... H04W 4/90 607/5 |
| 2014/0046393 A1* | 2/2014 | Sullivan ............... A61N 1/3904 607/7 |
| 2014/0070957 A1 | 3/2014 | Longinotti-Buitoni et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0265845 A1* | 9/2015 | Sullivan ............... A61N 1/3975 607/8 |
| 2015/0328472 A1 | 11/2015 | Sullivan et al. |
| 2016/0004831 A1 | 1/2016 | Carlson et al. |
| 2016/0082277 A1 | 3/2016 | Foshee, Jr. et al. |

OTHER PUBLICATIONS

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

Metting Van Rijn, A. C., Peper A., & Grimbergen, C. A., High-Quality Recording of Bioelectric Events Part 1: Interference Reduction, Theory and Practice, Review, Medical & Biological Engineering & Computing, Sep. 1990, pp. 389-397, IFMBE.

Pagan-Carlo, et al., "Encircling Overlapping Multipulse Shock Waveforms for Transthoracic Defibrillation," JACC Journals, Dec. 1998, vol. 32 Issue 7, p. 2065-2071.

* cited by examiner

WEARABLE CARDIOVERTER DEFIBRILLATOR (WCD) WITH BYSTANDER VOICE INTERACTION

RELATED APPLICATION

This application claims benefit of priority to U.S. Provisional Patent Application Ser. No. 63/111,957, filed on Nov. 10, 2020, titled WCD WITH BYSTANDER VOICE INTERACTION, which is incorporated herein by reference in its entirety for all purposes.

INFORMATION

Unless otherwise indicated herein, the approaches described in this section are not prior art to the claims in this application and are not admitted to be prior art by inclusion in this section.

Technology has contributed to improvements in healthcare. Some examples include healthcare related devices that may be mobile and personal. Mobile and personal healthcare devices may include Wearable Medical Devices (WMDs). Some WMDs may include medical devices that facilitate monitoring and treatment of various health related activities of a person. For example, a WMD may include a medical device that may be used to monitor a person's heart activity, including treatment of the heart. The heart activity monitored by the WMD may be in the form of electrical signals (i.e., electrocardiogram or ECG). Treatment of the heart may be in the form of a defibrillating shock, which may be administered responsive to the monitoring detecting a condition to trigger the treatment.

A WMD may be in a mobile form factor such as, but not limited to, a wearable support structure capable of being worn by a person, whose heart activity is to be monitored and/or treated. Having the WMD in a mobile form factor may facilitate continuous monitoring of a person's ECG, which may facilitate detection of heart related issues, including treatment of the heart related issues. Additionally, having the WMD in the mobile form factor wearable by the person may facilitate tracking of physical activities of the person wearing the WMD (e.g., steps).

WCDs are generally designed to detect and treat patients who experience ventricular tachycardia (VT)/ventricular fibrillation (VF) cardiac arrest, but there are some conditions that they cannot treat. WCDs currently used to treat patients generally do not know if bystanders are present.

All subject matter discussed in this section of this document is not necessarily prior art and may not be presumed to be prior art simply because it is presented in this section. Plus, any reference to any prior art in this description is not and should not be taken as an acknowledgement or any form of suggestion that such prior art forms parts of the common general knowledge in any art in any country. Along these lines, any recognition of problems in the prior art are discussed in this section or associated with such subject matter should not be treated as prior art, unless expressly stated to be prior art. Rather, the discussion of any subject matter in this section should be treated as part of the approach taken towards the particular problem by the inventor(s). This approach in and of itself may also be inventive. Accordingly, the foregoing summary is illustrative only and not intended to be in any way limiting. In addition to the illustrative aspects, embodiments, and features described above, further aspects, embodiments, and features will become apparent by reference to the drawings and the following detailed description.

SUMMARY

This Summary is provided to introduce a selection of concepts in simplified form that are further described below in the Detailed Description. This Summary is not intended to identify key or essential features or combinations of the claimed subject matter, nor is it intended to be used to limit the scope of the claimed subject matter.

A Wearable Medical Device (WMD) is designed to detect and treat patients who experience ventricular tachycardia (VT)/ventricular fibrillation (VF) cardiac arrest. There are other emergency cardiac conditions that a WCD can detect but not treat. For example, a WCD can detect asystole and severe bradycardia, but current WCDs have no ability to treat those conditions. Patients experiencing asystole, severe bradycardia, or pulseless electrical activity (PEA) quickly lose consciousness and may die if prompt treatment is not provided. To help the patient, a bystander needs to call emergency medical personnel (e.g., Emergency Medical Services (EMS)) and/or provide cardiopulmonary resuscitation (CPR) until help arrives. However, WMDs generally do not know if bystanders are present. Also, bystanders may be reluctant to help and/or may not know how to help. Even in cases where a WMD may be configured to request that bystanders who may be present provide CPR, the bystanders who are present and hear the request may not understand what to do and/or may not realize that prompts are directed at them. Embodiments of the present disclosure provide solutions to these and other technical problems described herein.

In accordance with one example embodiment provided to illustrate the broader concepts, systems, and techniques described herein, a wearable cardioverter defibrillator (WCD) system includes a support structure, the support structure configured to be worn by a subject such as a person (e.g., a patient). The WCD also includes a consciousness detection module configured to determine whether the subject wearing the support structure is unconscious. The WCD further includes an interactive bystander module configured to, responsive to a determination that the subject wearing the support structure is unconscious, generate a first voice prompt inquiring as to a presence of a bystander.

According to another illustrative embodiment provided to illustrate the broader concepts described herein, a method for interacting with a bystander to render assistance to a subject wearing a wearable cardioverter defibrillator (WCD) includes determining, by a WCD, whether a subject wearing the WCD is unconscious. The method also includes, responsive to a determination that the subject wearing the WCD is unconscious, generating, by the WCD, a first voice prompt inquiring as to a presence of a bystander.

According to another illustrative embodiment provided to illustrate the broader concepts described herein, a wearable cardioverter defibrillator (WCD) includes one or more non-transitory machine-readable mediums configured to store instructions and one or more processors configured to execute the instructions stored on the one or more non-transitory machine-readable mediums. Execution of the instructions causes the one or more processors to determine whether a subject wearing the WCD is unconscious. Execution of the instructions further causes the one or more processors to, responsive to a determination that the subject wearing the WCD is unconscious, generate a first voice prompt inquiring as to a presence of a bystander.

The foregoing summary is illustrative only and not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

In the drawings.

DETAILED DESCRIPTION

Figure 1:
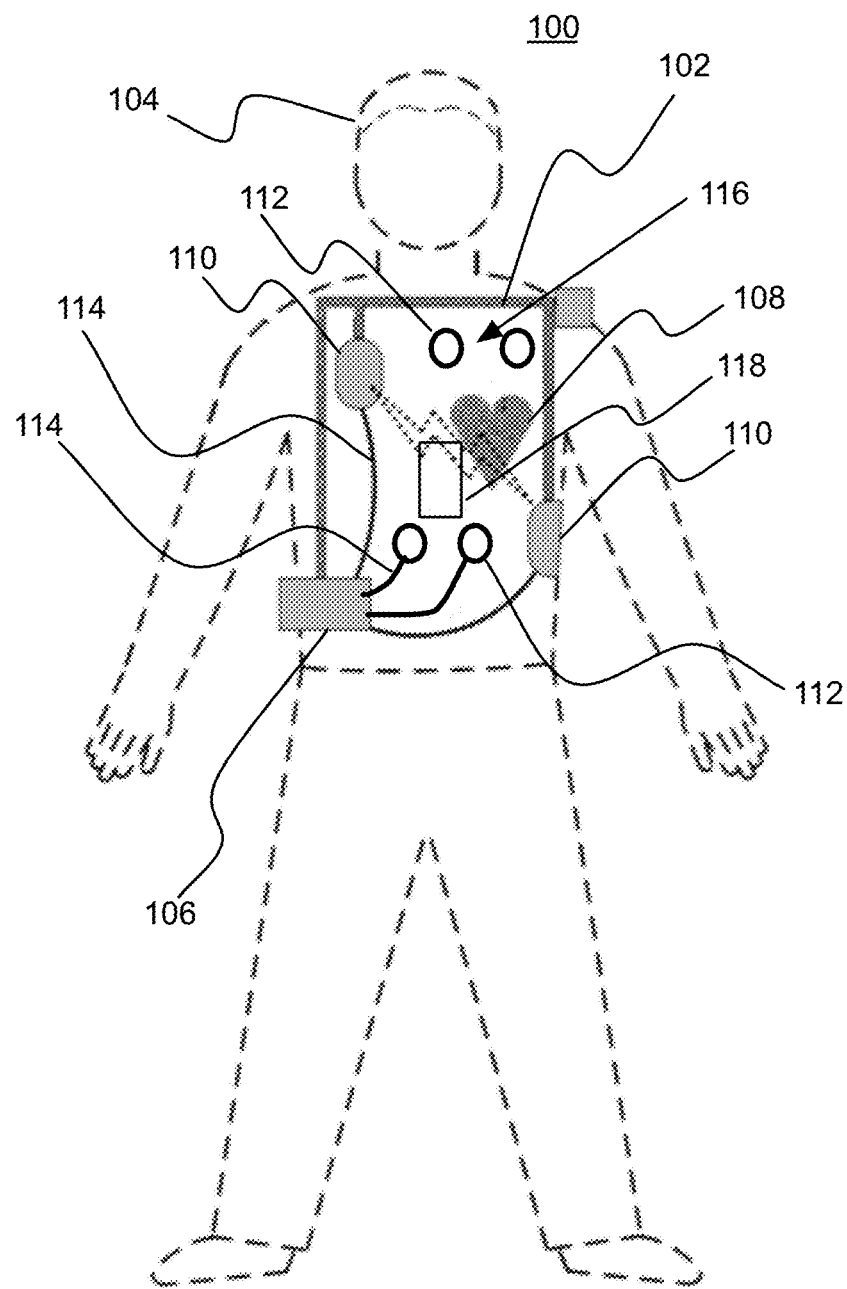
FIG. 1 illustrates a wearable cardioverter defibrillator (WCD), in accordance with various embodiments.

The following description sets forth various examples along with specific details to provide a thorough understanding of claimed subject matter. It will be understood by those skilled in the art after review and understanding of the present disclosure, however, that claimed subject matter may be practiced without some or more of the specific details disclosed herein. Further, in some circumstances, well-known methods, procedures, systems, components and/or circuits have not been described in detail in order to avoid unnecessarily obscuring claimed subject matter.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

This disclosure is drawn, inter alia, to apparatus and systems related to a wearable medical device (WMD) including an interactive bystander module configured to detect and/or interact with one or more bystanders (e.g., persons who is present in the vicinity of a subject wearing the WMD). For example, in some embodiments, the WMD can be configured to recruit one or more bystanders to help or otherwise assist a subject such as a person wearing the WMD in response to detecting that the person has or is experiencing a condition (e.g., medical condition) that the WMD is not able to treat.

In the present disclosure, a WMD may include a medical device that may be configured to facilitate monitoring and treatment of potential issues with a person's heart (i.e., the person may have a health condition, where the electrical control system of the heart may malfunction causing the heart to beat irregularly or not at all). Commonly, these types of medical devices may include a defibrillator device (e.g., a wearable cardioverter defibrillator or WCD). In the present disclosure, the WCD may include one or more motion sensors. Accordingly, the disclosure will be described referencing medical devices having one or more motion sensors, in accordance with various embodiments.

Briefly, the above mentioned issue with the rate of the heartbeat may be generally referred to as arrhythmia. Arrhythmia may be caused by many factors, but in general, arrhythmia may be caused by a malfunction in the electrical control system of the heart. Some types of arrhythmias may result in inadequate blood flow resulting in reduction or lack of the amount of blood pumped to the various parts of the body. For example, issues with the sinoatrial (SA) node may lead to arrhythmia of some kind. Some arrhythmias may lead to a condition known as sudden cardiac arrest (SCA). In an SCA condition, the heart may fail to pump blood effectively, and as a result, death may occur.

An example type of arrhythmia, which may be associated with SCA, may be a condition known as ventricular fibrillation (VF). VF may be a condition where a ventricle or ventricles, which make up the heart to facilitate the pumping of blood, may make uncoordinated movements instead of steady rhythmic movements. In the VF condition, the heart may not pump adequate amounts of blood or may not pump blood at all, which may eventually lead to death. Another type of arrhythmia, which may be associated with SCA, may be a condition known as ventricular tachycardia (VT).

Turning back to the medical device configured to be utilized to help treat VF by defibrillating the heart, the medical device may be capable of monitoring the electrical signals of the person's heart, and if necessary, administer therapy to the heart in the form of an electric shock. The medical device may monitor the electrical signals and provide the electric shock to the heart externally (i.e., through the surface of a body) via components commonly known as electrodes. The medical device may be in the form of a cardioverter defibrillator. The medical device may be included in a support structure configured to be worn by the person. In this example, the medical device may help facilitate monitoring the electrical activities of the person's heart and providing the electric shock to the heart in the VF condition. As a result, the medical device may help prevent Sudden Cardiac Death (SCD).

In some embodiments, the medical device may include one or more motion sensors to detect motion and orientation of the WMD worn by a person facilitating determination of a wellness of the person. For example, the medical device may include motion sensors implemented utilizing one or more accelerometers such as, but not limited to, the implementations disclosed in US Pat. App. Pub. No. US20190209853A1, filed on Oct. 11, 2018, titled "DETECTING WALKING IN A WEARABLE CARDIOVERTER DEFIBRILLATOR SYSTEM" ("853 app"), which is incorporated by reference in its entirety for all purposes.

In some embodiments, the medical device may include an interactive bystander module that can generate and issue voice messages to determine whether there is a bystander. For example, the interactive bystander module can generate a voice prompt asking any bystander proximate to the subject to provide a verbal response. In some embodiments, the interactive bystander module may generate the voice prompt upon the medical device determining that the person wearing the medical device may be or is unconscious. Additionally or alternatively, the interactive bystander module may generate the voice prompt upon the medical device determining that the person wearing the medical device may be experiencing a medical condition. In any case, generating a voice prompt in this way allows the medical device to determine whether there is a bystander. Determining whether bystanders are present allows the medical device to encourage bystanders who may be present to render assistance to the person.

For example, according to some embodiments, the interactive bystander module can issue a voice message stating that the person wearing the medical device is experiencing a medical condition (e.g., having a cardiac arrest) and then issue voice messages in an interactive way, with subsequent voice messages being based on responses (or lack of responses) by one or more bystanders. In some embodiments, the interactive bystander module may implement a "persona" to interact with bystanders to better engage with the bystander(s), prompt the bystanders to answer questions and/or provide information, recognize and answer questions from bystanders, convince reluctant bystanders to assist the person, and/or encourage helping bystanders to continue to provide assistance (e.g., provide CPR chest compressions).

Before to turning the figures, a non-limiting example scenario may be described. In the non-limiting example scenario, a subject, such as a person, may have a medical condition (e.g., heart condition), where the person may utilize a wearable medical device (WMD). The WMD may be configured to facilitate monitoring and treatment of the person's medical condition such as, but not limited to, a wearable cardioverter defibrillator (WCD). In one example, the WCD may include one or more detection modules to allow the WCD to facilitate detection of consciousness/unconsciousness of the person and/or medical condition being experienced by the person. In accordance with various embodiments disclosed herein, the WCD may be configured to detect and/or interact with one or more bystanders upon determining that the person is unconscious, likely unconscious, and/or experiencing a medical condition.

In the non-limiting scenario, the person may be wearing the WCD. The person wearing the WCD may experience an arrhythmia and lose consciousness. The WCD may be configured to issue a voice prompt or message such as "Are bystanders present?" upon detecting that the person is experiencing an arrhythmia and/or has lost consciousness. In some embodiments, the WCD may issue such a voice prompt subsequent to providing an appropriate medical procedure, such as a shock delivery process, for example.

In embodiments, the WCD can include a voice recognition program or module that is configured to listen for an affirmative audible response such as, "Yes," or "Yeah." In embodiments, the voice recognition module is intelligent enough to detect/accept/recognize a wide range of affirmative responses. In some embodiments, the voice recognition program or module can implement and/or utilize artificial intelligence (AI) training techniques to accept/recognize the wide range of affirmative audible responses. For example, the voice recognition module can be implemented similarly to automated attendants used in customer service "bots" or voice assistant such as those implemented in some smartphones (e.g., Siri).

Continuing with the non-limiting scenario, in one example, the WCD may determine that a bystander is present. For example, the WCD may determine that a bystander is present upon detecting an affirmative audible response (e.g., "Yes") from the bystander in response to the generated voice message "Are bystanders present?" In response to determining the presence of a bystander, the WCD may generate a voice inquiry asking the bystander to indicate whether the bystander is willing to assist (aid) the person. For example, the WCD can issue a voice inquiry such as "Hi, are you willing to help this person?" By asking a question to bystanders the WCD makes it clear that the WCD is talking to (communicating with) a specific bystander. Also, further instructions that may be generated by the WCD would then be understood to be directed at the bystander that responded. If the WCD simply issued a bystander command without first establishing communication, it is possible bystanders could be confused. The bystanders may not realize that the command was directed at them. However, embodiments of the present disclosure enable the WCD to ask a question first to clarify who the commands are directed at and what the commands will be.

With continued reference to the non-limiting scenario, the WCD may determine that the bystander is not willing to assist the person. For example, the WCD may determine that the bystander is unwilling to render assistance upon detecting a negative audible response (e.g., "No") from the bystander in response to the generated voice inquiry "Hi, are you willing to help this person?" In response to determining that the bystander is unwilling to render assistance, the WCD may determine whether there are other bystanders. For example, the WCD may issue a voice prompt or message such as "Are other bystanders present?"

On the other hand, if the WCD determines that the bystander is willing to render assistance (e.g., by detecting an affirmative audible response, e.g., "Yes", from the bystander in response to the generated voice inquiry "Hi, are you willing to help this person?"), the WCD may generate a voice prompt asking the bystander to indicate whether emergency medical personnel has been contacted. For example, the WCD can issue a voice inquiry such as "Has someone called 911?" If the WCD determines that emergency medical personnel has not been contacted (e.g., by detecting a negative audible response, e.g., "No", from the bystander in response to the generated voice inquiry "Has someone called 911?"), the WCD may generate a voice message to the bystander(s) to contact emergency medical personnel. For example, the WCD can issue a voice command such as "Please call 911 immediately."

Otherwise, if the WCD recognizes an affirmative response to the question "Has someone called 911?" (i.e., that a bystander has already called 911), then the WCD can issue a voice message to direct the bystander to perform a medical procedure based on a detected medical condition being experienced by the parson (e.g., to perform CPR chest compressions based on determining that the person is experiencing arrhythmia). In some embodiments, the WCD can also provide instructions on how to perform the medical procedure (e.g., provide CPR instructions for performing proper CPR, e.g., according to American Heart Association guidelines). In some such embodiments, the WCD may also provide a metronome to aid the bystander to perform chest compressions at a proper rate.

In some embodiments, the WCD may be configured to recognize situations in which it is helpful for the WCD to ask one or more questions of bystanders. For example, some current WCDs can analyze a patient's ECG signal, but cannot readily discern whether the patient is conscious. A patient can reply to a question if he or she is conscious, but not if he or she is unconscious. And even if conscious the patient may not be able to respond due to some other condition. According to some embodiments of the present disclosure, the WCD may be configured to issue a voice message to bystanders asking whether a person wearing the WCD is conscious or unconscious. The WCD can then perform one or more appropriate procedures based on the bystander's response to the question. For example, if the bystander's response is that the person is conscious, the WCD can abort or suspend a medical procedure that is currently being applied to the person (e.g., abort or suspend a shock delivery process).

On the other hand, if the bystander's response is that the person is unconscious, the WCD can proceed with a medical procedure application decision process (e.g., the shock-no shock decision process) knowing that the person is unconscious. In this way, the WCD is able to improve the accuracy of the medical procedure application decision. For example, if the WCD establishes that the patient is unconscious, the WCD can utilize an ECG analysis to assess whether a shock should be delivered, or CPR given to the person. For instance, rhythms with a heart rate below the normal shock threshold may be given a shock if the person is known to be unconscious. For example, a WCD that normally would only shock rhythms with a heart rate higher than 170 BPM may shock a person who is conscious and has a heart rate above 130 BPM. A person who has a lower rate can be given CPR.

In another example, and according to an embodiment, there may also be situations in which a person wearing a WCD is impaired and may need help from a bystander. For example, if the person has or is experiencing a stroke, the person may not be able to respond, for example to questions issued by the WCD, and may need a bystander to contact emergency medical personnel (e.g., call 911). In some embodiments, the WCD may be configured to issue voice message(s) asking the person and/or a bystander a series of questions that may help to establish the person's condition. For example, the WCD can generate one or more voice inquiries asking whether the person has numbness or weakness in the face, arm, or leg, especially on one side of the body. If the WCD does not recognize the person's voice response, it may be because the person is disoriented (confused) or having difficulty speaking due to the stroke. In some embodiments, the WCD may be configured to recognize a bystander responding to the questions instead. For example, the WCD may be configured to recognize the voice of the person wearing the WCD. In this way, the WCD can differentiate between the voice of the person wearing the WCD and a different voice (e.g., the voice of a bystander). In some embodiments, the WCD can ask the bystander whether the person seems confused, has trouble speaking, or difficulty understanding speech. If the WCD determines that a stroke was likely, for example based on the monitoring of the person and/or the response from the bystander, the WCD can request the bystander to contact emergency medical personnel (e.g., call 911).

In another example, and according to an embodiment, a person wearing a WCD may also be impaired by trauma such as a fall, a car crash, or other accident. In some embodiments, the WCD can include an accelerometer, which the WCD monitors to detect whether the WCD has experienced a sudden jolt indicative of a fall, accident, etc. In response to such a detection, the WCD can issue one or more voice messages asking bystander(s) questions to discern whether an accident actually occurred and/or whether emergency medical personnel should be called.

It will be appreciated that embodiments of the present disclosure may advantageously overcome problems that current WCDs can experience. For example, WCDs that only issue voice messages can suffer from a lack of bystander response. In contrast, the automated interactive WCD "persona" may improve the active engagement/responsiveness of bystanders by asking questions or making requests, recognizing bystander responses to the questions or requests, and in turn responding to the bystander responses in a meaningful way.

Turning now to the figures, FIG. 1 illustrates a wearable medical device (WMD), in accordance with various embodiments. In FIG. 1, a WMD may be configured to facilitate monitoring and treatment of a person's heart such as, but not limited to, a wearable cardioverter defibrillator (WCD) 100. The WCD 100 may be included in a support structure 102, which may be configured to be worn by a person 104. The WCD 100 may include various electronic components to facilitate the functionality of the WCD 100 as a heart monitoring and defibrillator device. The various electronic components may be illustrated as a WCD module (hereon a WCD monitor 106). The WCD 100 may include two therapy electrodes configured to defibrillate a person's heart 108, defibrillator electrodes 110, and a number of monitoring electrodes 112 configured to detect and measure the person's electrical heart activity (e.g., electrocardiogram or ECG). As shown, the monitoring electrodes 112 and the defibrillator electrodes 110 may be located proximate to the person's heart 108 and chest area 116. The monitoring electrodes 112 and the defibrillator electrodes 110 may be communicatively coupled to the WCD monitor 106 via a number of electrical leads 114. Additionally, shown in FIG. 1, the support structure may be configured to facilitate inclusion of one or more motion sensors (hereon, motion sensor 118). The motion sensor 118 may be communicatively coupled to the WCD monitor 106 via wired or wireless communication methodologies.

As described herein, the motion sensor 118, included in the support structure 102, may be configured to detect motion in accordance with various embodiments. Examples of a motion sensor may include accelerometers, where the accelerometers may be configured to measure acceleration and/or orientation relative to gravity along 3 orthogonal axes. Some additional examples of a motion sensor may include 9-axis absolute orientation sensor, which may have a combination of 3-axis acceleration sensor, a 3-axis gyroscope, and a 3-axis geomagnetic sensor. A 9-axis absolute orientation sensor may be of the kind available from Bosch Sensortec GmbH of Reutlingen, Germany. In addition to the various axis related sensors, some other example motion sensor may include global positioning system (GPS) components and/or barometer components. Further, the motion sensor 118 may include force, pressure, inertial, velocity, and position sensors such as, but not limited to, those sensors available from Sensoria, Inc., of Redmond, Washington. Accordingly, the claimed subject matter is not limited in this respect.

In FIG. 1, when the person 104 moves while wearing the WCD 100, the motion sensor 118 may detect the motion and transmit the signal to the WCD monitor 106 to be processed. As will be described in more detail with respect to FIG. 3, the WCD monitor 106 may include various electronic components, including one or more processors, configured to implement the various examples claimed and disclosed herein.

Figure 2:
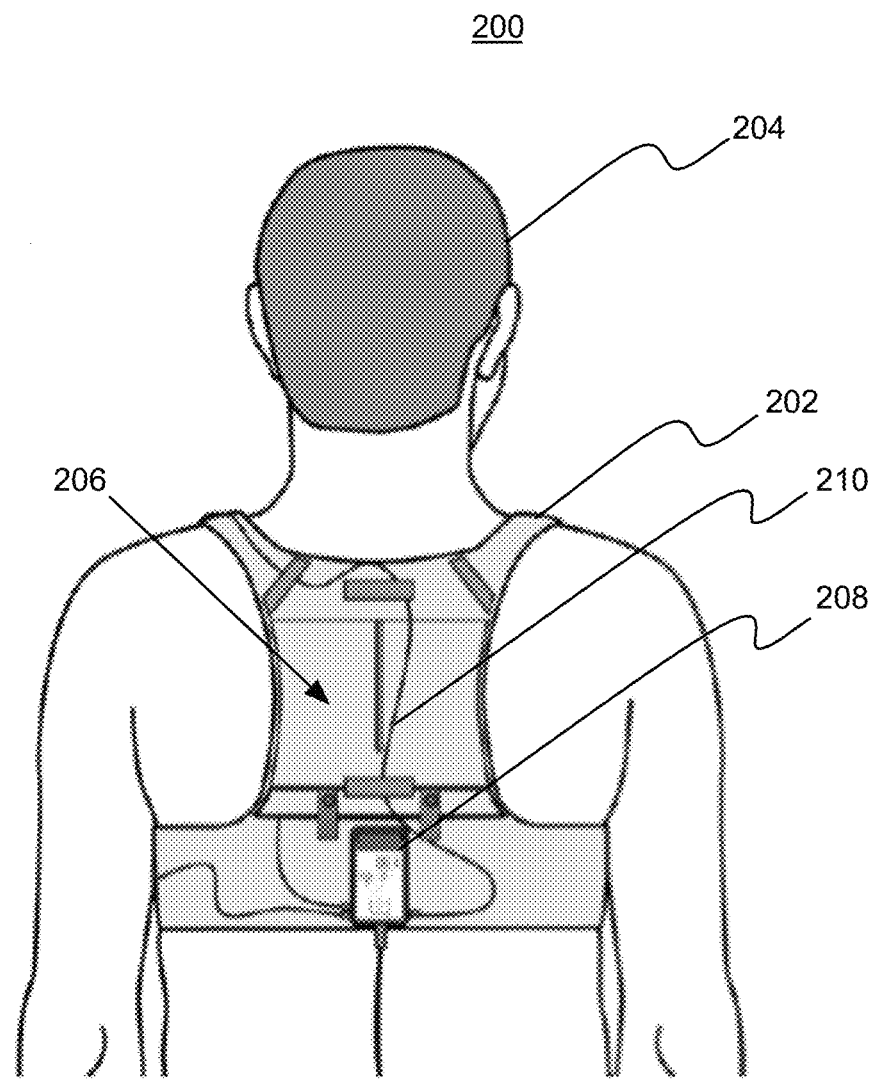
FIG. 2 illustrates a back view of a WCD, in accordance with various embodiments.

FIG. 2 illustrates a back view of a WCD, in accordance with various embodiments. In FIG. 2, a WCD 200 may be configured to be included in a support structure 202 configured to be worn by a person 204. The support structure 202 may have a back side 206. The back side 206 may be configured to accommodate a motion sensor 208. Additionally, shown in FIG. 2, one or more electrical leads 210 may be included in the support structure 202 to facilitate communicatively coupling the motion sensor 208 with a WCD monitor (e.g., shown in FIG. 1). As will be described in more detail, as the person 204 moves (e.g., walk), the motion sensor 208 may detect the motion including intensity. The detected motion sensor 208 may be communicated to the WCD to be processed in accordance with various embodiments.

In FIG. 2, even though the motion sensor 208 may be shown as being proximately located at the back side 206 of the person 204, the location of the motion sensor 208 may be a variety of locations such as, but not limited to a front side, left or right side, and so forth. Additionally, the motion sensor 208 may be located separately from a WCD monitor (e.g., WCD monitor 106 shown in FIG. 1). However, in some embodiments, the motion sensor 208 may be included in a WCD monitor and may be a component of a WCD monitor. Accordingly, the claimed subject matter is not limited in this respect.

Figure 3:
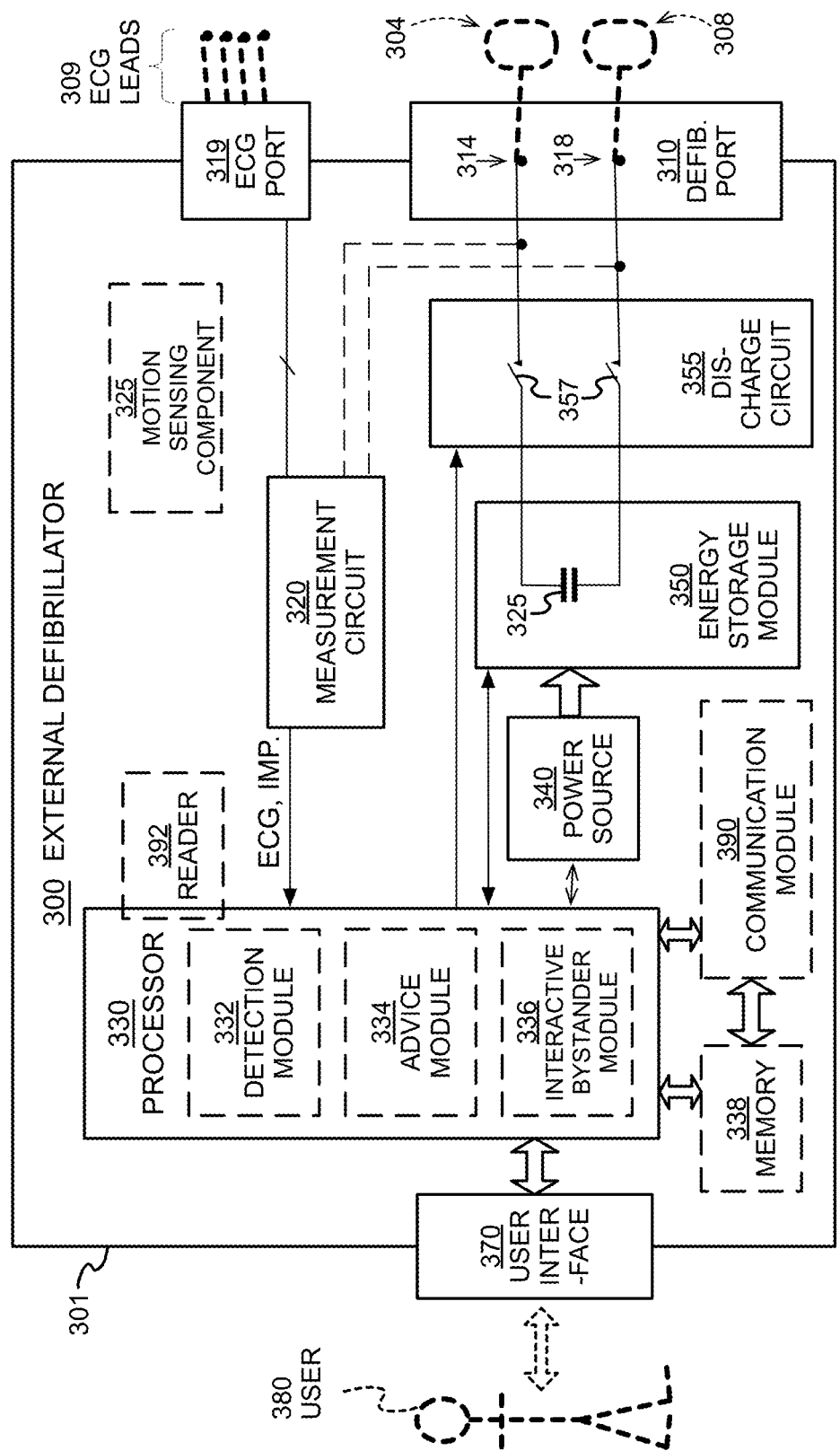
FIG. 3 is a block diagram illustrating components of reconfigurable medical device, in accordance with various embodiments.

FIG. 3 is a block diagram illustrating components of reconfigurable medical device, in accordance with various embodiments. These components may be, for example, components of medical device such as, but not limited to, a WCD 100 and 200 (shown in FIGS. 1 and 2).

The defibrillator device 300 may be some of the above examples of a one or more modules for the medical device intended for use by a user 380 (e.g., a wearer, a person, a patient, etc.). The defibrillator device 300 may typically include a defibrillation port 310, such as a socket in housing 301. The defibrillation port 310 may include nodes 314 and 318. One or more electrodes 304 and 308, which may be removably plugged into the defibrillation port 310, so as to make electrical contact with nodes 314 and 318, respectively. It may also be possible that the electrodes 304 and 308 may be connected continuously to the defibrillation port 310, etc. Either way, the defibrillation port 310 may be used for guiding via the electrodes 304 and 308 to a person 304 an electrical charge that may have been stored in the defibrillator device 300, as described herein.

The defibrillator device 300 may also have an ECG port 319 in the housing 301, for receiving ECG cables 309. The ECG cables 309 may facilitate sensing of an ECG signal (e.g., a 12-lead signal or from a different number of lead signals). Moreover, a defibrillator-monitor could have additional ports (not shown) making the defibrillator device 300 more reconfigurable, and a motion sensing component 325 may be configured to detect motion of a physical activity and may include one or more motion sensors as described herein. In some examples, there may be additional components configured to filter the ECG signal (e.g., application of at least one filter to the signal to help facilitate removal of artifacts such as, but not limited to, chest compression due to chest compressions being delivered to the person).

The defibrillator 300 also may include a measurement circuit 320. The measurement circuit 320 may receive physiological signals from the ECG port 319, and also from other ports, if provided. The circuit 320 may render detected physiological signals and their corresponding information. The information may be in the form of data, or other signals, etc.

The measurement circuit 320 may obtain physiological signals through the nodes 314 and 318, when the electrodes 304 and 308 are attached to the person. In these cases, a person's ECG signal may be detected as a voltage difference between the electrodes 304 and 308. Additionally, the impedance between the electrodes 304 and 308 may be detected, among other things, whether the electrodes 304 and 308 have been inadvertently disconnected from the person.

The defibrillator 300 may also include a processor 330. The processor 330 may be implemented in a wide variety of manners for causing actions and operations to be performed. Some examples may include digital and/or analog processors such as microprocessors and digital-signal processors (DSPs), controllers such as microcontrollers, software running in a machine environment, programmable circuits such as Field Programmable Gate Arrays (FPGAs), Field-Programmable Analog Arrays (FPAAs), Programmable Logic Devices (PLDs), Application Specific Integrated Circuits (ASICs), and so on or any combination thereof.

The processor 330 may include a number of modules. One example module may be a detection module 332, which may detect outputs from the measurement circuit 320. The detection module 332 may include a VF detector. Accordingly, the person's detected ECG may be utilized to help determine whether the person is experiencing ventricular fibrillation (VF).

In another example module may be an advice module 334, which may provide advice based, at least in part, on outputs of detection module 332. The advice module 334 may include an algorithm such as, but not limited to, Shock Advisory Algorithm, implement decision rules, and so on. For example, the advice may be to shock, to not shock, to administer other forms of therapy, and so on. If the advice is to shock, some defibrillator examples may report the advice to the user, and prompt them to do it. In other examples, the defibrillator device may execute the advice by administering the shock. If the advice is to administer CPR, the defibrillator 300 may further issue prompts for administrating CPR, and so forth.

The processor 330 may include additional modules, such as interactive bystander module 336 for various bystander voice interactive related functions described herein. Additionally, if other motion sensing component 325 is provided, it may be operated in part by processor 330, etc.

In an example, the defibrillator device 300 may include a memory 338, which may work together with the processor 330. The memory 338 may be implemented in a wide variety of manners. For example, the memory 338 may be implemented such as, but not limited to, nonvolatile memories (NVM), read-only memories (ROM), random access memories (RAM), and so forth or any combination thereof. The memory 338 may include programs for the processor 330, and so on. The programs may include operational programs execution by the processor 330 and may also include protocols and methodologies that decisions may be made by advice module 334. Additionally, the memory 338 may store various prompts for the user 380, etc. Moreover, the memory 338 may store a wide variety of information (i.e., data) such as, but not limited to information regarding the person.

The defibrillator 300 may also include a power source 340. In order to facilitate portability of defibrillator device 300, the power source 340 may include a battery type device. A battery type device may be implemented as a battery pack, which may be rechargeable or not be rechargeable. At times, a combination of rechargeable and non-rechargeable battery packs may be utilized. Additionally, the power source may be configured to be modified to accommodate the power level demands (e.g., monitoring mode without therapy or vice versa). Examples of power source 340 may include AC power override, where AC power may be available, and so on. In some examples, the processor 330 may control the power source 340.

Additionally, the defibrillator device 300 may include a configurable energy storage module 350. The configurable energy storage module 350 may be configured to store some electrical energy (e.g., when preparing for sudden discharge to administer a shock). The configurable energy storage module 350 may be charged from the power source 740 to an appropriate level of energy, as may be controlled by the processor 330. In some implementations, the configurable energy storage module 350 may include one or more capacitors 352, and the like.

The defibrillator 300 may include a discharge circuit 355. The discharge circuit 355 may be controlled to facilitate discharging of the energy stored in energy storage module 350 to the nodes 314 and 318, and also to electrodes 304 and 308. The discharge circuit 355 may include one or more switches 357. The one or more switches 357 may be configured in a number of manners such as, but not limited to, an H-bridge, and so forth.

The defibrillator device 300 may further include a user interface 370 for the user 380. The user interface 370 may be implemented in a variety of manners. For example, the user interface 370 may include a display screen capable of displaying what is detected and measured, provide visual feedback to the user 380 for their resuscitation attempts, and so forth. The user interface 370 may also include an audio output such as, but not limited to, a speaker to issue audio prompts, etc. The user interface 370 may additionally include various control devices such as, but not limited to, pushbuttons, touch display, and so forth. Additionally, the discharge circuit 355 may be controlled by the processor 330 or directly by the user 380 via the user interface 370, and so forth.

Additionally, the defibrillator device 300 may include other components. For example, a communication module 390 may be provided for communicating with other machines and/or the electrodes. Such communication may be performed wirelessly, or via wire, or by infrared communication, and so forth. Accordingly, information may be communicated, such as person data, incident information, therapy attempted, CPR performance, ECG information, and so forth.

The above described components may be configured and reconfigured, in accordance with various embodiments. For example, monitoring mode or monitoring and therapy mode.

Figure 4:
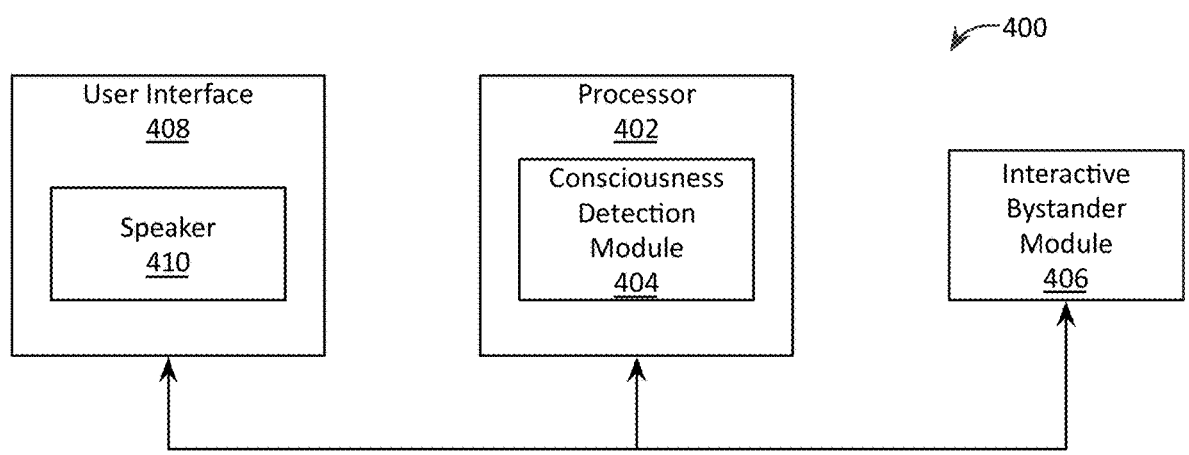
FIG. 4 is a block diagram illustrating selective components of a system for detecting and interacting with a bystander, in accordance with various embodiments.

FIG. 4 is a block diagram illustrating selective components of a system 400 for detecting and interacting with a bystander, in accordance with various embodiments. The system 400 may be included as various modules as shown in FIG. 3 (e.g., Interactive Bystander Module 336. As shown, system 400 may include a processor 402, an interactive bystander module 406, and a user interface 408 communicatively coupled to one another, for example, via a communication link or other suitable interconnection. In embodiments, system 400 may be included in or implemented as part of a WMD such as, for example, WCD 100 of FIG. 1, WCD 200 of FIG. 2, and WCD 300 of FIG. 3. In some implementation, one or more components of system 400 may be implemented as separate components (e.g., external components) communicatively coupled to the WMD. For example, interactive bystander module 406 may be located external to the WMD, while being communicatively coupled to the WMD. System 400 can include various other hardware and software components which, for the sake of clarity, are not shown in FIG. 4. As will be appreciated, numerous configurations can be implemented and the present disclosure is not intended to be limited to any particular one.

Processor 402 may be implemented by one or more programmable processors to execute one or more executable instructions, such as a computer program, to perform the functions of a system (e.g., system 400). As used herein, the term "processor" describes circuitry that performs a function, an operation, or a sequence of operations. The function, operation, or sequence of operations may be hard coded into the circuitry or soft coded by way of instructions held in a memory device and executed by the circuitry. A processor may perform the function, operation, or sequence of operations using digital values and/or using analog signals. In some embodiments, processor 402 may be substantially similar to processor 330 described above in the context of FIG. 3.

As can be seen in FIG. 4, processor 402 may include a consciousness detection module 404. Consciousness detection module 404 can determine a consciousness of a subject such as a person. For example, when a person is wearing a WMD (e.g., WCD 100 of FIG. 1, WCD 200 of FIG. 2, and WCD 300 of FIG. 3) in which system 400 is implemented, consciousness detection module 404 can determine whether the person is conscious, unconscious, and/or likely unconscious. In some implementations, consciousness detection module 404 make such determinations based on outputs from one or more components of the WMD, such as, for example, measurement circuit 320, motion sensing component 325, and/or detection module 332 of WCD 300 of FIG. 3. For example, if the output of motion sensing component 325 indicates a lack of motion or activity for a predetermined duration and the output of measurement circuit 320 indicates a medical condition, consciousness detection module 404 can determine that the person is unconscious or likely unconscious. As another example, if the output of motion sensing component 325 indicates motion or activity, consciousness detection module 404 can determine that the person is conscious. As another example, if the output of detection module 332 indicates the person is experiencing a severe arrhythmia and the output of motion sensing component 325 indicates a lack of motion or activity, consciousness detection module 404 can determine that the person is unconscious. In some embodiments, consciousness detection module 404 may be substantially similar to detection module 332 described above in the context of FIG. 3.

Severe arrythmia may include conditions such as, but not limited to, VF, high rate VT, asystole, severe bradycardia, and so forth. For example, a high rate VT may include variation of the heart beat from approximately 150 beats per minute (BPM) to approximately 200 BPM. On the other hand, a severe bradycardia may include variation of the heart beat from approximately 20 BPM to approximately 50 BPM. Accordingly, the claimed subject matter is not limited in these respects.

Determination of the person being unconscious may include detection of changes in the physical activity of the person or lack of physical activity/motion. For example, the WMD (e.g., WCD 100 of FIG. 1, WCD 200 of FIG. 2, and WCD 300 of FIG. 3) may be configured to detect variations in impedance by utilizing the electrodes (e.g., 112 of FIG. 1). Variations in impedance may correspond to indication of motion of the person. An example of a variation may include ECG artifacts that may indicate motion. Additionally, a common-mode voltage shift may indicate motion. Accordingly, if the person is unconscious, the person may likely not be moving, which may be determined by any of the aforementioned methodologies.

Still referring to system 400 of FIG. 4, user interface 408 can be made in many ways according to various embodiments. User interface 408 may include input/output devices, which can be visual, audible, or tactile, for communicating to a user (e.g., a person wearing the WMD or and/or one or more bystanders) by outputting images, sounds, or vibrations. Images, sounds, vibrations, and anything that can be perceived by the user can also be called human perceptible indications. There are many examples of output devices. For example, as can be seen in FIG. 4, one example output device is a speaker 410. Speaker 410 may be used to issue voice prompts, voice messages, and other forms and types of audible sounds to communicate with the person wearing the WMD and/or one or more bystanders. For example, speaker 410 can be used to issue the voice prompts, voice messages, etc., generated by the interactive bystander module (e.g., interactive bystander module 406) of the WMD as described in the above non-limiting scenarios and otherwise variously described herein.

In brief, interactive bystander module 406 may be configured to generate voice messages to determine and encourage one or more bystanders to render assistance to a person wearing the WMD. The generated voice messages can be issued via a speaker (e.g., speaker 410). In some embodiments, interactive bystander module 406 can generate such voice messages upon detecting or otherwise determining certain conditions of the person wearing the WMD. For example, interactive bystander module 406 determine the person's condition based on the output of consciousness detection module 404. For example, in an implementation, upon determining that the person is unconscious, consciousness detection module 404 can send or otherwise provide to interactive bystander module 406 an indication that the person is unconscious. In response, consciousness detection module 404 can generate a voice message to determine whether there is a bystander. For example, interactive bystander module 406 can generate a voice prompt asking any bystander to provide a verbal response to the prompt.

In some embodiments, interactive bystander module 406 can generate such voice messages upon determining the presence of a bystander and/or a willingness of the bystander to render assistance to the person. For example, if it is determined that a bystander is present, interactive bystander module 406 can generate a voice inquiry asking the bystander to indicate whether the bystander is willing to assist the person. If it is determined that the bystander is not willing or cannot assist the person, interactive bystander module 406 can generate a voice message to determine whether there is another bystander. If it is determined that the bystander is willing or can assist the person, interactive bystander module 406 can generate a voice prompt asking the bystander to indicate whether emergency medical personnel has been contacted. If it is determined that emergency medical personnel has not been contacted, interactive bystander module 406 can a voice message directed to the bystander to contact emergency medical personnel.

As will be appreciated, interactive bystander module 406 can also generate other voice messages/inquiries/prompts to identify a bystander or bystanders and to interact with the bystander to encourage and guide the bystander to render assistance to a person wearing the WMD in addition to the examples of voice messages/prompts provided in the context of FIG. 4. For example, interactive bystander module 406 can generate voice messages and prompts as described in the above non-limiting scenarios and otherwise variously described herein.

In some further examples, the interactive bystander module 406 may be configured to interact with the bystander at a more personal level. For example, if the interactive bystander module 406 is interacting with a bystander who is willing to assist/help, the interactive bystander module 406 may ask for the name of the bystander. That is, the interactive bystander module 406 may be configured to perform voice recognition to say "Hello John Doe. Thank you for assisting. John Doe, have you or someone called 911?" In accordance with some embodiments, the interactive bystander module 406 may include machine learning capabilities (i.e., artificial intelligence/AI).

Figure 5:
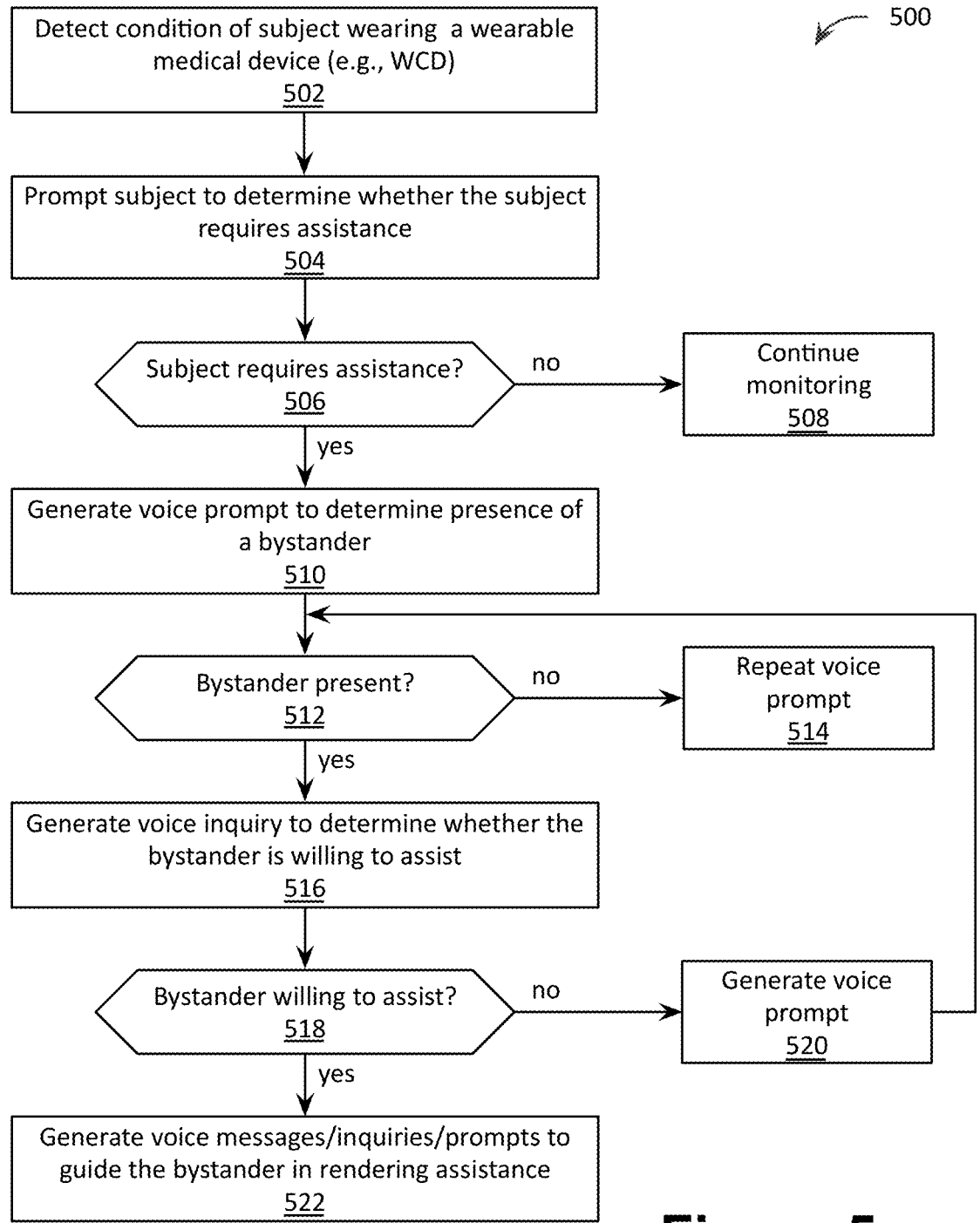
FIG. 5 is a flow diagram of an illustrative process for guiding a bystander to render assistance to a subject wearing a wearable medical device (WMD), in accordance with various embodiments of the present disclosure.

FIG. 5 is a flow diagram of an illustrative process 500 for guiding a bystander to render assistance to a subject wearing a wearable medical device (WMD), in accordance with various embodiments of the present disclosure. Process 500 may be implemented or performed by any suitable hardware, or combination of hardware and software, including without limitation WCD 100 of FIG. 1, WCD 200 of FIG. 2, WCD 300 of FIG. 3, system 400 of FIG. 4, or a combination thereof. For example, in some embodiments, the operations, functions, or actions illustrated in process 500 may be performed, for example, in whole or in part by consciousness detection module 404, interactive bystander module 406, and speaker 410, or any combination of these including other components of system 400 described with respect to FIG. 4.

With reference to process 500 of FIG. 5, and in an illustrative use case, at block 502, interactive bystander module 404 can detect a condition of a subject such as a person who is wearing the WMD (e.g., a WCD). For example, the condition of the subject can be indicated or otherwise provided by consciousness detection module 404. In this example use case, the detected condition may be a condition in which the subject may require assistance. For example, consciousness detection module 404 may indicate that the subject may be experiencing a stroke. As another example, consciousness detection module 404 may indicate that the subject may be involved in an accident.

At block 504, interactive bystander module 406 can determine whether the subject requires assistance. For example, interactive bystander module 406 can generate a voice message asking the subject whether he or she needs assistance (e.g., assuming that the name of the subject is "John", a voice message such as "John, do you need assistance?"). The voice message can be issued via speaker 410.

If, at block 506, interactive bystander module 406 determines that the subject does not require assistance, then at block 508, interactive bystander module 406 can continuing monitoring for conditions in which the subject may require assistance. For example, interactive bystander module 406 can determine that the subject does not require assistance based on a detecting an audible response from the subject ("No, I do not need assistance.").

Otherwise, if, at block 506, interactive bystander module 406 determines that the subject does require assistance, then at block 510, interactive bystander module 406 can generate a voice prompt to determine whether there is a bystander. For example, interactive bystander module 406 can determine that the subject does require assistance based on a lack of response from the subject or a disoriented response from the subject. In some cases, interactive bystander module 406 can determine that the subject does require assistance based on determining that the subject is experiencing a medical issue or condition. In any case, upon determining that the subject requires assistance, interactive bystander module 406 can generate a voice prompt inquiring as to a presence of a bystander (e.g., "Is there anyone present?").

If, at block 512, interactive bystander module 406 determines that a bystander is not present, then at block 514, interactive bystander module 406 can repeat the voice prompt inquiring as to a presence of a bystander (e.g., "This person needs assistance right away. Is there anyone present?").

Otherwise, if, at block 512, interactive bystander module 406 determines that a bystander is present, then at block 516, interactive bystander module 406 can generate a voice inquiry to determine whether the bystander is willing to assist the subject (e.g., "Thank you for responding. Are you willing to help this person?").

If, at block 518, interactive bystander module 406 determines that the bystander is not willing to render assistance to the subject, then at block 520, interactive bystander module 406 can a voice prompt to determine whether there is another bystander (e.g., "This person needs assistance right away. Is there anyone else present?"). Interactive bystander module 406 can then determine, at block 512, whether there is another bystander who is present.

If, at block 518, interactive bystander module 406 determines that the bystander is willing to render assistance to the subject, then at block 522, interactive bystander module 406 can generate voice messages/inquires/prompts to guide the bystander in rendering assistance to the subject. For example, interactive bystander module 406 can generate voice messages/inquires/prompts to guide the bystander as previously described herein.

FURTHER EXAMPLE EMBODIMENTS

The following examples pertain to further embodiments, from which numerous permutations and configurations will be apparent.

Example 1 includes a wearable cardioverter defibrillator (WCD) system including: a support structure, the support structure configured to be worn by a subject; a consciousness detection module configured to determine whether the subject wearing the support structure is unconscious; and an interactive bystander module configured to, responsive to a determination that the subject wearing the support structure is unconscious, generate a first voice prompt inquiring as to a presence of a bystander.

Example 2 includes the subject matter of Example 1, wherein the first voice prompt informs of a medical condition being experienced by the subject wearing the support structure.

Example 3 includes the subject matter of any of Examples 1 and 2, wherein the interactive bystander module is further configured to determine the presence of the bystander.

Example 4 includes the subject matter of Example 3, wherein the determination of the presence of the bystander is based on an audible response from the bystander.

Example 5 includes the subject matter of any of Examples 3 and 4, wherein the interactive bystander module is further configured to, responsive to the determination of the presence of the bystander, generate a voice inquiry asking the bystander to indicate whether the bystander is willing to assist the subject wearing the support structure.

Example 6 includes the subject matter of Example 5, wherein the interactive bystander module is further configured to, responsive to a determination that the bystander is not willing to assist the subject wearing the support structure, generate a second voice prompt inquiring as to a presence of another bystander.

Example 7 includes the subject matter of Example 5, wherein the interactive bystander module is further configured to, responsive to a determination that the bystander is willing to assist the subject wearing the support structure, generate a third voice prompt asking the bystander to indicate whether emergency medical personnel has been contacted.

Example 8 includes the subject matter of Example 7, wherein the interactive bystander module is further configured to, responsive to a determination that emergency medical personnel has not been contacted, generate a fourth voice prompt asking the bystander to contact emergency medical personnel.

Example 9 includes the subject matter of Example 7, wherein the interactive bystander module is further configured to, responsive to a determination that emergency medical personnel has not been contacted, cause the WCD system to contact emergency medical personnel.

Example 10 includes the subject matter of Example 7, wherein the interactive bystander module is further configured to, responsive to a determination that emergency medical personnel has been contacted, cause the WCD system to not contact emergency medical personnel.

Example 11 includes the subject matter of Example 5, wherein the interactive bystander module is further configured to, responsive to a determination that the bystander is willing to assist the subject wearing the support structure, generate a fifth voice prompt asking the bystander to indicate whether the subject wearing the support structure is conscious or unconscious.

Example 12 includes the subject matter of Example 11, wherein the interactive bystander module is further configured to, responsive to a determination that the subject wearing the support structure is conscious based on an audible response from the bystander, cause the WCD system to abort or suspend a shock delivery process.

Example 13 includes the subject matter of Example 5, wherein the interactive bystander module is further configured to, responsive to a determination that the bystander is willing to assist the subject wearing the support structure: cause the WCD system to determine a medical condition of the subject wearing the support structure; and generate one or more voice messages providing instructions to the bystander on how to perform a medical procedure based on the determined medical condition of the subject wearing the support structure.

Example 14 includes the subject matter of any of Examples 1 through 13, wherein the determination that the subject wearing the support structure is unconscious is based on detection of a slurred response to a prompt to the subject wearing the support structure to indicate whether the subject is experiencing a medical condition.

Example 15 includes the subject matter of any of Examples 1 through 14, wherein the determination that the subject wearing the support structure is unconscious is based on detection of a lack of motion of the subject wearing the support structure for a predetermined duration.

Example 16 includes a method for interacting with a bystander to render assistance to a subject wearing a wearable cardioverter defibrillator (WCD), the method including: determining, by a WCD, whether a subject wearing the WCD is unconscious; and, responsive to a determination that the subject wearing the WCD is unconscious, generating, by the WCD, a first voice prompt inquiring as to a presence of a bystander.

Example 17 includes the subject matter of Example 16, wherein the first voice prompt informs of a medical condition being experienced by the subject wearing the WCD.

Example 18 includes the subject matter of any of Examples 16 and 17, further including, responsive to a determination of a presence of a bystander, generating, by the WCD, a voice inquiry asking the bystander to indicate whether the bystander is willing to assist the subject wearing the WCD.

Example 19 includes the subject matter of Example 18, further including, responsive to a determination that the bystander is not willing to assist the subject wearing the WCD, generating, by the WCD, a second voice prompt inquiring as to a presence of another bystander.

Example 20 includes the subject matter of Example 18, further including, responsive to a determination that the bystander is willing to assist the subject wearing the WCD, generating, by the WCD, a third voice prompt asking the bystander to indicate whether emergency medical personnel has been contacted.

Example 21 includes the subject matter of Example 20, further including, responsive to a determination that emergency medical personnel has not been contacted, generating, by the WCD, a fourth voice prompt asking the bystander to contact emergency medical personnel.

Example 22 includes the subject matter of Example 20, further including, responsive to a determination that emergency medical personnel has not been contacted, contacting, by the WCD, emergency medical personnel.

Example 23 includes the subject matter of Example 18, further including, responsive to a determination that the bystander is willing to assist the subject wearing the WCD, generating, by the WCD, a fifth voice prompt asking the bystander to indicate whether the subject wearing the WCD is conscious or unconscious.

Example 24 includes the subject matter of Example 23, further including, responsive to a determination that the subject wearing the WCD is conscious, aborting or suspending, by the WCD, a shock delivery process, wherein the determination that the subject wearing the WCD is conscious is based on an audible response from the bystander.

Example 25 includes the subject matter of Example 18, further including, responsive to a determination that the bystander is willing to assist the subject wearing the WCD: determining, by the WCD, a medical condition of the subject wearing the WCD; and generating, by the WCD, one or more voice messages providing instructions to the bystander on how to perform a medical procedure based on the determined medical condition of the subject wearing the WCD.

Example 26 includes the subject matter of any of Examples 16 through 25, further including: prompting, by the WCD, the subject wearing the WCD to indicate whether the subject is experiencing a medical condition; receiving, by the WCD, an audible response from the subject; and receiving, by the WCD, an audible response from the subject; wherein the determination that the subject wearing the WCD is unconscious is based on a determination that the audible response from the subject is a slurred response.

Example 27 includes the subject matter of any of Examples 16 through 26, further including determining, by the WCD, a lack of motion of the subject wearing the WCD for a predetermined duration, wherein the determination that the subject wearing the WCD is unconscious is based on a determination of a lack of motion of the subject wearing the WCD for a predetermined duration.

Example 28 includes a wearable cardioverter defibrillator (WCD) including one or more non-transitory machine-readable mediums configured to store instructions and one or more processors configured to execute the instructions stored on the one or more non-transitory machine-readable mediums, wherein execution of the instructions causes the one or more processors to: determine whether a subject wearing the WCD is unconscious; and, responsive to a determination that the subject wearing the WCD is unconscious, generate a first voice prompt inquiring as to a presence of a bystander.

Example 29 includes the subject matter of Example 28, wherein the first voice prompt informs of a medical condition being experienced by the subject wearing the WCD.

Example 30 includes the subject matter of any of Examples 28 and 29, wherein execution of the instructions further causes the one or more processors to determine the presence of the bystander.

Example 31 includes the subject matter of Example 30, wherein the determination of the presence of the bystander is based on an audible response from the bystander.

Example 32 includes the subject matter of any of Examples 30 and 31, wherein execution of the instructions further causes the one or more processors to, responsive to the determination of the presence of the bystander, generate a voice inquiry asking the bystander to indicate whether the bystander is willing to assist the subject wearing the WCD.

Example 33 includes the subject matter of Example 32, wherein execution of the instructions further causes the one or more processors to, responsive to a determination that the bystander is not willing to assist the subject wearing the WCD, generate a second voice prompt inquiring as to a presence of another bystander.

Example 34 includes the subject matter of Example 32, wherein execution of the instructions further causes the one or more processors to, responsive to a determination that the bystander is willing to assist the subject wearing the WCD, generate a third voice prompt asking the bystander to indicate whether emergency medical personnel has been contacted.

Example 35 includes the subject matter of Example 34, wherein execution of the instructions further causes the one or more processors to, responsive to a determination that emergency medical personnel has not been contacted, generate a fourth voice prompt asking the bystander to contact emergency medical personnel.

Example 36 includes the subject matter of Example 34, wherein execution of the instructions further causes the one or more processors to, responsive to a determination that emergency medical personnel has not been contacted, contact emergency medical personnel.

Example 37 includes the subject matter of Example 34, wherein execution of the instructions further causes the one or more processors to, responsive to a determination that emergency medical personnel has been contacted, not contact emergency medical personnel.

Example 38 includes the subject matter of Example 32, wherein execution of the instructions further causes the one or more processors to, responsive to a determination that the bystander is willing to assist the subject wearing the WCD, generate a fifth voice prompt asking the bystander to indicate whether the subject wearing the WCD is conscious or unconscious.

Example 39 includes the subject matter of Example 38, wherein execution of the instructions further causes the one or more processors to, responsive to a determination that the subject wearing the WCD is conscious based on an audible response from the bystander, abort or suspend a shock delivery process.

Example 40 includes the subject matter of Example 32, wherein execution of the instructions further causes the one or more processors to, responsive to a determination that the bystander is willing to assist the subject wearing the WCD: determine a medical condition of the subject wearing the WCD; and generate one or more voice messages providing instructions to the bystander on how to perform a medical procedure based on the determined medical condition of the subject wearing the WCD.

Example 41 includes the subject matter of any of Examples 28 through 40, wherein the determination that the subject wearing the WCD is unconscious is based on detection of a slurred response to a prompt to the subject wearing the WCD to indicate whether the subject is experiencing a medical condition.

Example 42 includes the subject matter of any of Examples 28 through 41, wherein the determination that the subject wearing the WCD is unconscious is based on detection of a lack of motion of the subject wearing the WCD for a predetermined duration.

It should be appreciated after review of this disclosure that it is contemplated within the scope and spirit of the present disclosure that the claimed subject matter may include a wide variety of healthcare devices. Accordingly, the claimed subject matter is not limited in these respects.

As will be further appreciated in light of this disclosure, with respect to the processes and methods disclosed herein, the functions performed in the processes and methods may be implemented in differing order. Additionally or alternatively, two or more operations may be performed at the same time or otherwise in an overlapping contemporaneous fashion. Furthermore, the outlined actions and operations are only provided as examples, and some of the actions and operations may be optional, combined into fewer actions and operations, or expanded into additional actions and operations without detracting from the essence of the disclosed embodiments.

As used in the present disclosure, the terms "engine" or "module" or "component" may refer to specific hardware implementations configured to perform the actions of the engine or module or component and/or software objects or software routines that may be stored on and/or executed by general purpose hardware (e.g., computer-readable media, processing devices, etc.) of the computing system. In some embodiments, the different components, modules, engines, and services described in the present disclosure may be implemented as objects or processes that execute on the computing system (e.g., as separate threads). While some of the system and methods described in the present disclosure are generally described as being implemented in software (stored on and/or executed by general purpose hardware), specific hardware implementations, firmware implements, or any combination thereof are also possible and contemplated. In this description, a "computing entity" may be any computing system as previously described in the present disclosure, or any module or combination of modulates executing on a computing system.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Reference in the specification to "an implementation," "one implementation," "some implementations," or "other implementations" may mean that a particular feature, structure, or characteristic described in connection with one or more implementations may be included in at least some implementations, but not necessarily in all implementations. The various appearances of "an implementation," "one implementation," or "some implementations" in the preceding description are not necessarily all referring to the same implementations.

While certain exemplary techniques have been described and shown herein using various methods and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter is not limited to the particular examples disclosed, but that such claimed subject matter also may include all implementations falling within the scope of the appended claims, and equivalents thereof.

What is claimed:

1. A wearable cardioverter defibrillator (WCD) system comprising:
   a support structure, the support structure configured to be worn by a subject;
   a consciousness detection module configured to determine whether the subject wearing the support structure is unconscious; and
   an interactive bystander module configured to:
      responsive to a determination that the subject wearing the support structure is unconscious, generate a first voice prompt inquiring as to a presence of a bystander;
      responsive to a determination of the presence of the bystander, generate a voice inquiry asking the bystander to indicate whether the bystander is willing to assist the subject wearing the support structure; and
      responsive to a determination that the bystander is not willing to assist the subject wearing the support structure, generate a second voice prompt inquiring as to a presence of another bystander.

2. The WCD system of claim 1, wherein the first voice prompt informs of a medical condition being experienced by the subject wearing the support structure.

3. The WCD system of claim 1, wherein the determination of the presence of the bystander is based on an audible response from the bystander.

4. The WCD system of claim 1, wherein the interactive bystander module is further configured to, responsive to a determination that the bystander is willing to assist the subject wearing the support structure, generate a third voice prompt asking the bystander to indicate whether emergency medical personnel has been contacted.

5. The WCD system of claim 4, wherein the interactive bystander module is further configured to, responsive to a determination that the emergency medical personnel has not been contacted, generate a fourth voice prompt asking the bystander to contact the emergency medical personnel.

6. The WCD system of claim 4, wherein the interactive bystander module is further configured to, responsive to a determination that the emergency medical personnel has not been contacted, cause the WCD system to contact the emergency medical personnel.

7. The WCD system of claim 4, wherein the interactive bystander module is further configured to, responsive to a determination that the emergency medical personnel has been contacted, cause the WCD system to not contact the emergency medical personnel.

8. The WCD system of claim 1, wherein the interactive bystander module is further configured to, responsive to a determination that the bystander is willing to assist the subject wearing the support structure, generate a fifth voice prompt asking the bystander to indicate whether the subject wearing the support structure is conscious or unconscious.

9. The WCD system of claim 8, wherein the interactive bystander module is further configured to, responsive to a determination that the subject wearing the support structure is conscious based on an audible response from the bystander, cause the WCD system to abort or suspend a shock delivery process.

10. The WCD system of claim 1, wherein the interactive bystander module is further configured to, responsive to a determination that the bystander is willing to assist the subject wearing the support structure:
    cause the WCD system to determine a medical condition of the subject wearing the support structure; and
    generate one or more voice messages providing instructions to the bystander on how to perform a medical procedure based on the determined medical condition of the subject wearing the support structure.

11. The WCD system of claim 1, wherein the determination that the subject wearing the support structure is unconscious is based on detection of a slurred response to a prompt to the subject wearing the support structure to indicate whether the subject is experiencing a medical condition.

12. The WCD system of claim 1, wherein the determination that the subject wearing the support structure is unconscious is based on detection of a lack of motion of the subject wearing the support structure for a predetermined duration.

13. A method for interacting with a bystander to render assistance to a subject wearing a wearable cardioverter defibrillator (WCD), the method comprising:
    determining, by the WCD, whether the subject wearing the WCD is unconscious;
    responsive to a determination that the subject wearing the WCD is unconscious, generating, by the WCD, a first voice prompt inquiring as to a presence of the bystander;
    responsive to a determination of the presence of the bystander, generating a voice inquiry asking the bystander to indicate whether the bystander is willing to assist the subject wearing the WCD; and
    responsive to a determination that the bystander is not willing to assist the subject wearing the WCD, generating a second voice prompt inquiring as to a presence of another bystander.

14. The method of claim 13, wherein the first voice prompt informs of a medical condition being experienced by the subject wearing the WCD.

15. The method of claim 13, further comprising, responsive to a determination that the bystander is willing to assist the subject wearing the WCD, generating, by the WCD, a third voice prompt asking the bystander to indicate whether emergency medical personnel has been contacted.

16. The method of claim 13, further comprising, responsive to a determination that the bystander is willing to assist the subject wearing the WCD:
    determining, by the WCD, a medical condition of the subject wearing the WCD; and
    generating, by the WCD, one or more voice messages providing instructions to the bystander on how to perform a medical procedure based on the determined medical condition of the subject wearing the WCD.

17. The method of claim 13, further comprising:
    prompting, by the WCD, the subject wearing the WCD to indicate whether the subject is experiencing a medical condition;
    receiving, by the WCD, an audible response from the subject; and
    determining, by the WCD, that the audible response from the subject is a slurred response, wherein the determination that the subject wearing the WCD is unconscious is based on the determination that the audible response from the subject is the slurred response.

18. The method of claim 13, further comprising determining, by the WCD, a lack of motion of the subject wearing the WCD for a predetermined duration, wherein the determination that the subject wearing the WCD is unconscious is based on the determination of the lack of motion of the subject wearing the WCD for the predetermined duration.

* * * * *